(12) United States Patent
Hartlep et al.

(10) Patent No.: US 7,892,224 B2
(45) Date of Patent: Feb. 22, 2011

(54) INVERSE CATHETER PLANNING

(75) Inventors: Andreas Hartlep, Naring (DE); Christoph Pedain, Munich (DE)

(73) Assignee: BrainLAB AG, Feldkirchen (DE)

( * ) Notice: Subject to any disclaimer, the term of this patent is extended or adjusted under 35 U.S.C. 154(b) by 1269 days.

(21) Appl. No.: 11/421,583

(22) Filed: Jun. 1, 2006

(65) Prior Publication Data

US 2007/0016012 A1    Jan. 18, 2007

Related U.S. Application Data

(60) Provisional application No. 60/689,987, filed on Jun. 13, 2005.

(30) Foreign Application Priority Data

Jun. 1, 2005    (EP) .................................. 05011788

(51) Int. Cl.
*G06Q 50/00* (2006.01)
(52) U.S. Cl. ......................................................... 606/2
(58) Field of Classification Search ....................... 705/2
See application file for complete search history.

(56) References Cited

U.S. PATENT DOCUMENTS

| | | | |
|---|---|---|---|
| 5,638,819 A | 6/1997 | Manwaring et al. | |
| 6,061,587 A * | 5/2000 | Kucharczyk et al. | 600/411 |
| 6,214,019 B1 * | 4/2001 | Manwaring et al. | 606/130 |
| 6,381,483 B1 * | 4/2002 | Hareyama et al. | 600/407 |
| 7,313,430 B2 * | 12/2007 | Urquhart et al. | 600/429 |
| 7,505,807 B1 * | 3/2009 | Kucharczyk et al. | 600/411 |

(Continued)

FOREIGN PATENT DOCUMENTS

EP    1 102 229 A3    11/2000

(Continued)

OTHER PUBLICATIONS

Dannen, V. et al. "Accurrate Localization of Needle Entry Point in Interventional MRI". Journal of Magnetic Resonance Imaging, vol. 12, 2000. p. 645-649.*

*Primary Examiner*—Luke Gilligan
*Assistant Examiner*—Robert Sorey
(74) *Attorney, Agent, or Firm*—Renner, Otto, Boisselle & Sklar, LLP

(57) ABSTRACT

A method for determining and representing possible entry and/or target areas for positioning catheters in an area on the basis of functional data and/or structural and/or anatomical data of the area, includes: indicating at least one entry area of the catheter or at least one target area of the catheter; determining at least one target area of the catheter based on the at least one indicated entry area of the catheter and taking into consideration specified catheter positioning guidelines and the functional data and/or structural and/or anatomical data of the area, or at least one entry area of the catheter based on the at least one indicated target area of the catheter and taking into consideration specified catheter positioning guidelines and the functional data and/or structural and/or anatomical data of the area; and representing the functional data and/or structural and/or anatomical data with the at least one indicated entry area and the at least one determined target area, or representing the functional data and/or structural and/or anatomical data with the at least one indicated target area and the at least one determined entry area.

24 Claims, 2 Drawing Sheets

U.S. PATENT DOCUMENTS

| | | | |
|---|---|---|---|
| 7,599,730 B2 * | 10/2009 | Hunter et al. | 600/424 |
| 2004/0010221 A1 | 1/2004 | Pedain et al. | |
| 2004/0106934 A1 * | 6/2004 | Grossman | 606/130 |
| 2007/0249911 A1 * | 10/2007 | Simon | 600/300 |

FOREIGN PATENT DOCUMENTS

| | | |
|---|---|---|
| EP | 1 103 229 A2 | 11/2000 |
| EP | 1 374 790 A1 | 6/2002 |
| WO | 97/31581 | 9/1997 |

* cited by examiner

INVERSE CATHETER PLANNING

RELATED APPLICATION DATA

This application claims priority of U.S. Provisional Application No. 60/689,987 filed on Jun. 13, 2005, which is incorporated herein by reference in its entirety.

FIELD OF THE INVENTION

The present invention relates to a method and device for determining and representing possible entry and/or target areas for positioning one or more catheters in an area, in particular in tissue regions such as a brain, wherein the area is determined on the basis of structural and/or anatomical data of the area.

BACKGROUND OF THE INVENTION

In known methods for positioning one or more catheters, the catheters are positioned on the basis of simple catheter positioning guidelines. In keeping with these guidelines, the catheter tip is often positioned sufficiently deep in a brain region and positioned at a sufficient distance from surfaces to make an infusion agent dispensed from the catheter less likely to discharge into hollows, sulci or back into the cerebral cortex. However, the guidelines specified are individually adjusted for different patients and tissue regions, such that a uniform diffusion of the infusion agent into given regions cannot be ensured and also such that discharge cannot be sufficiently prevented. Furthermore, when planning positions for one or more catheters, the guidelines are complicated and time-consuming to implement in an individual patient anatomy, since for each catheter entry point and for each corresponding catheter end point, the corresponding guidelines are gauged and manually checked, for example, using a suitable computer program.

SUMMARY OF THE INVENTION

One or more target areas of one or more catheters are determined from a specified entry area, and conversely, a preferred entry area of one or more catheters is determined from a specified target area of a catheter. The determined areas also can be represented together with structural and/or anatomical data. Thus, a multitude of suitable target or entry points can be determined (e.g., by a computer program) for each input entry or target point. In determining the suitable points, specified or computed guidelines may be taken into consideration (e.g., guidelines for positioning catheters), wherein corresponding guidelines (e.g., guidelines for positioning catheters) are implemented semi-automatically.

A method for determining and representing possible entry and/or target areas for positioning one or more catheters in an area, such as a particular tissue (e.g., a brain or brain region or a body part), is performed on the basis of functional data and/or structural and/or anatomical data of the area, such as the brain or brain region. The functional data and/or structural and/or anatomical data of the area can be captured using given imaging methods, in particular medical imaging methods such as computer tomography, nuclear spin tomography, ultrasound, positron emission tomography or single photon emission computed tomography (SPECT), and can be determined before or while the method is being performed. At least one entry area or one entry region of the catheter in the area, such as for example the brain or brain region, can be input, for example, by means of a data input device such as a keyboard, mouse or touch screen, or at least one target area or one target region of the catheter in the area, such as the brain or the brain region, can be indicated or specified by a user.

Taking into consideration the functional data and/or structural and/or anatomical data of the area, determined for example previously, and taking into consideration catheter positioning guidelines which, for example, may be specified or selected, such as particular distance characteristics of the catheter or catheters from each other or from characteristic areas such as a surface or particular tissue sections of the area or the distance from vessels and/or risk structures, at least one target area of the catheter or the catheter tip or a catheter section can be determined from the at least one entry area which is indicated or specified (e.g., selected by a user or determined automatically or by chance). The entry area of the catheter is then the zone in which the catheter may be inserted or introduced into the area, and the target area is the zone which or the vicinity of which the catheter or the catheter tip or a defined catheter section may be ultimately intended to reach, in order to ensure that an infusion agent is dispensed into the target area, such as cancer cells or tumors, for example.

Conversely, instead of the entry area of the catheter or the catheter tip, the target area, for example, can be automatically determined and specified or indicated by a user, wherein at least one suitable and/or possible or optimal entry area is determined from the at least one indicated target area, taking into consideration the defined or specified catheter positioning guidelines and the determined functional data and/or structural and/or anatomical data of the area. If, for example, the determined or known functional data and/or structural and/or anatomical data are represented on a data output device, such as a screen or a touch screen, and a preferred entry area of the catheter is indicated or selected and represented on the data output device, then once the associated or optimal target area has been determined or once all the possible target areas have been determined, the determined target area or areas can be represented on the data output device such that one or more preferred target areas could be selected by a user (e.g., when a number of possible target areas are output or represented). Conversely, the functional data and/or structural and/or anatomical data of the area and a selected or indicated target area can be represented, wherein once the at least one associated, corresponding, suitable, possible or optimal entry area has been determined or calculated, the determined entry area or areas or entry region can be represented, in particular graphically.

In addition to the represented information, such as the at least one indicated or determined entry area or the at least one indicated or determined target area or the structural and/or anatomical data of the area, the catheter positioning guidelines taken into consideration in determining the target areas or entry areas of the catheter, such as for example specified or defined distance characteristics of the catheters from each other or the distances from the catheter or the catheter tip or catheter delivery sections to the characteristic areas, can also be represented.

Preferably, an entry point or entry points also can be selected or determined as the entry area or entry areas, wherein the entry points can lie inside an entry area, for example. A target point or target points also can be indicated or determined instead of or in addition to the target areas. In particular, one or more individual entry points can be specified, from which one or more corresponding or suitable or optimal target points can be determined, taking into consideration the structure and/or anatomy of the area and taking into consideration the catheter positioning guidelines. Preferably, one or more target areas also can be specified or selected by a user, for example, from which one or more associated, possible or suitable entry points can be determined. Preferably the specific anatomy, structure and/or function of the area are taken into consideration as well as the defined or specified catheter positioning guidelines.

Preferably, the at least one entry point or the at least one entry area also can be calculated iteratively from the at least one indicated target point or target area. Conversely, the at least one target point or the at least one target area can be iteratively determined from the at least one entry point or entry area.

Thus, for example, at least one entry area of the catheter can be initially indicated, with respect to which one or more associated or possible target areas or target points can be determined with the aid of the defined or selected catheter positioning guidelines and the determined structure and/or function and/or anatomy of the area. In particular, the optimal or most suitable target area or areas or target point or points can be represented, or all the possible target areas or target points can be represented, for example, such that one or more optimal or most suitable target areas or target points can be highlighted, or a user can select the desired or preferred one or more target points or target areas from the multitude of proposed target areas or target points.

Once the at least one possible or optimal target area or target point has been determined from the at least one entry area or entry point, all the entry areas or entry points, for example, can be calculated that correspond to the at least one determined target area or target point or which are possible or preferred taking into consideration the catheter positioning guidelines and the determined functional data and/or structural and/or anatomical data of the area. Preferably, the determined entry areas or entry points lie inside the initially indicated entry area or inside the initially indicated or specified entry areas. All the possible entry points or all the entry points corresponding to the determined target areas or target points also can be determined, wherein only those entry points are shown or represented that lie inside the initially indicated entry area or inside the specified entry areas or which lie in a particular zone around the initially indicated entry areas. All the possible entry points or all the entry points corresponding to the target point or target points, for example, also can be shown, taking into consideration suitable guidelines, wherein preferably only the most suitable entry point or points are highlighted or represented. All the possible entry points also can be determined, but only one or more entry points, most suitable taking into consideration the catheter positioning guidelines and the determined structure and/or function and/or anatomy of the area, may be represented.

Conversely, at least one target area or target point of the catheter can be initially selected or specified by a user, taking into consideration characteristic sizes, for example, wherein one or more entry areas or entry points can be determined with respect to each of the specified target areas or target points. Additionally, the one or more entry points can be determined only with respect to a part of the specified target areas or target points, wherein the catheter positioning guidelines and the determined or known structure and/or function and/or anatomy of the area may be taken into consideration in making the calculation or determination. With respect to the at least one determined possible entry area or entry point of the catheter, at least one entry point which is most suitable or optimal, taking into consideration, for example, the structure and/or anatomy and/or function of the area and the catheter positioning guidelines can be selected and represented. In particular, a number of entry points can be represented and, for example, only the most suitable entry point or points may be highlighted and shown.

Corresponding or associated target points, for example, then can be determined from the previously determined at least one possible entry point. Preferably, the target points are determined and shown that lie inside the previously indicated target area or areas or that lie inside a determined or specified zone around the target areas. Also, of the determined target points, only particular target points, for example the target points lying inside the specified target area or the most suitable target points, or also only the most suitable target point, can be shown, highlighted or represented.

Trajectories, movement or positioning specifications or courses of movement, which indicate or describe how the catheter can be moved from an at least one known or indicated entry area or entry point to the at least one determined target area or target point, also can be determined and represented. The movement, positioning specifications or courses of movement can indicate how the catheter may be optimally moved or positioned between the entry area and the target area, preferably taking into consideration the structure and/or the anatomy of the area and the catheter positioning guidelines.

Conversely, the trajectories, movement, positioning specifications or courses of movement also can describe how the catheter may be optimally moved or positioned between the at least one indicated or specified target area and the at least one determined entry area.

Preferably, the movement or positioning specifications are shown or graphically represented together with the specified or determined entry area or target area and/or the functional data and/or structural and/or anatomical data of the area and/or the catheter positioning guidelines. The movement or positioning specifications, for example, can be output as coordinates or shown or represented as a graphic representation such as arrows or movement vectors in or with the structural and/or anatomical data of the area.

After performing the method, the at least one catheter is preferably positioned such that there is a minimum distance or a minimized distance from the surface of the area, such as from the brain surface or from the characteristic zones of the area such as channels, hollows, sulci or ventricles, said distance satisfying the specified positioning guidelines.

Preferably, the catheter positioning guidelines from the European patent specification having the application number 04 009 835.2 are used, the teaching of which is incorporated by reference in its entirety. Three catheter positioning guidelines are preferably used. First, the distance between the catheter, the catheter tip or the catheter delivery section—or the distances between the multiple or additional catheters, catheter tips or catheter delivery sections—and the surface of the area into which the catheter or catheters has/have been inserted or introduced, should be between 1 and 4 cm, in particular 2.5 cm. Furthermore, the distances between a number of inserted catheters, catheter tips or catheter delivery sections and catheters, catheter tips or catheter delivery sections of other catheters should be at least 1 cm, preferably 3 cm. Also, the distance between the catheter, the catheter tip or the catheter delivery section—or, if a number of catheters are used, preferably the distance between all the catheters, all the catheter tips or all the catheter delivery sections—and particular characteristic sections of the area, such as particular tissue sections, in particular grooves, furrows, sulci, chambers, ventricles, hollows, recesses, holes and/or cavities of the area or tissue, should be between 2 and 15 mm, in particular 10 mm. Minimum possible distances between the catheter and characteristic zones or minimum possible distances between the catheters also can be used as catheter positioning guidelines.

The positioning guidelines also can be calculated dynamically and can be variable, depending, for example, on the respective anatomical, functional and/or structural position of the catheter, the target area and/or the entry area. The positioning guidelines also can be adapted to the respective catheter types, the infusion parameters and/or the infusate parameters.

A tissue or parts of a tissue, such as the brain or brain region, may be used as the area in which the catheter or catheters is/are to be positioned, wherein functional data and/or structural and/or anatomical data of the area or tissue can be recorded by means of a medical imaging method, such as computer tomography, nuclear spin tomography, ultrasound, positron emission tomography or SPECT tomography, before or during the method. Information on particular tissue parts or tissue sections and/or on areas of tissue parts removed by operations and/or areas of tissue deformities, tissue abnormalities or tissue anomalies, such as oedemas, and/or on particular characteristic anatomical areas such as the brain stem, can thus be determined before the method is performed and, therefore, can be known while the method is performed, or the information can be determined during or as part of the method. Information on the surface of the area or tissue and/or on grooves or furrows, gyri and sulci of the area or tissue, in particular furrows between the cerebral convolutions, and/or on chambers, ventricles of the area, tissue, hollows, recesses, holes and/or cavities of the area or tissue, which, for example, can be known or can be determined before or while the method is performed, also can be used as functional data and/or structural and/or anatomical data. With the aid of the obtained or known functional, structural and/or anatomical data, the diffusion or distribution of an infusion agent in the area or tissue, for example, can be determined or specified or predicted, or compliance with the catheter positioning guidelines can be monitored or controlled by means of the structural and/or anatomical data.

The invention further relates to a computer program which, when loaded onto a computer or running on a computer, performs a method as described above. The invention further relates to a program storage medium or computer program product comprising such a program.

A device for determining and representing possible entry areas and/or target areas for catheter positioning in an area on the basis of functional data and/or structural and/or anatomical data of the area, comprises a data input device such as a keyboard, mouse or touch screen, by means of which at least one entry area of a catheter or at least one target area of a catheter can be input or selected on a screen or touch screen via coordinates or by selecting or indicating an area. The selected entry area or target area or the selected areas, for example, can be indicated in color, or otherwise graphically highlighted, indicated or represented. User-defined catheter positioning guidelines, for example, also can be input into the device, or specified or defined catheter positioning guidelines can be individually altered via the data input device. Functional data and/or structural and/or anatomical data of the area, recorded by means of a medical imaging method such as a computer tomograph, nuclear spin tomograph, ultrasound tomograph, positron emission tomograph or SPECT tomograph, for example, also can be input into the device via the data input device and archived or stored, for example in a database.

Based on the indicated or selected target area or target areas of the catheter, and taking into consideration the catheter positioning guidelines stored in the database or input by a user, and taking into consideration the functional data and/or structural and/or anatomical data of the area or tissue, stored for example in the database or input by a user, at least one possible entry area of the catheter can be calculated in a computing unit, such as a processor or a computer, which can be connected to the data input device.

The computing unit, for example, also can determine that no possible entry area exists with respect to the indicated target area. A user also can be shown how many calculated entry areas deviate from the entry areas that may be used as possible or suitable entry areas, taking into consideration the catheter positioning guidelines and the structural and/or anatomical data. An audio signal or graphic output, for example, can indicate that it was not possible to determine a possible entry point.

By means of the computing unit, one or more target areas associated with an indicated or specified entry area, which, for example, has been selected by a user via a data input device, can be determined with the aid of the known or determined structure and/or function and/or anatomy of the area or tissue and with the aid of the stored or input catheter positioning guidelines.

The device further comprises a database that can be connected to the computing unit or integrated into the computing unit, and in which catheter positioning guidelines can be stored and/or in which individual functional data and/or structural and/or anatomical data of various areas or tissues or brains can be archived, for example. These data can be read by the computing unit and used to determine the target areas or target points or entry areas or entry points.

The device also comprises a data output device, such as a screen or a touch screen, which also can be used as a data input device, instead of or in addition to a data input device such as a keyboard. Preferably, the data output device is connected to the computing unit and/or to the database, such that, for example, the data output device can graphically represent the functional data and/or structural and/or anatomical data and/or can show the specified or selected catheter positioning guidelines, in particular within the graphically represented functional data and/or structural and/or anatomical data, and/or can show the at least one indicated or determined target area or the at least one indicated or determined entry area, in particular in the representation of the structure, function and anatomy of the area or tissue. The catheter positioning guidelines or the indicated or determined entry areas or target areas, for example, can be highlighted in color in the structure and/or the anatomy of the area, such that a user can easily select and/or identify the areas.

The device also can comprise a medical tracking system that can determine the position of the catheter or catheters and the position of the area or tissue. Preferably, the tracking system is connected to the computing unit or integrated into the computing unit, such that the tracking system can convey the information on the position of the catheter or catheters and on the position of the area or the tissue to the computing unit. The computing unit can correlate or link the information gained on the position of the catheters and of the area with the information on the structure and/or the anatomy of the area, or with the information on the entry areas or target areas, and can represent the correlated information on the data output device.

BRIEF DESCRIPTION OF THE DRAWINGS

The forgoing and other embodiments of the invention are hereinafter discussed with reference to the drawings.

FIG. 1a illustrates another exemplary determination of possible entry areas from a specified target point of the catheter, taking into consideration catheter positioning guidelines in accordance with the invention.

DETAILED DESCRIPTION

Figure 1A:
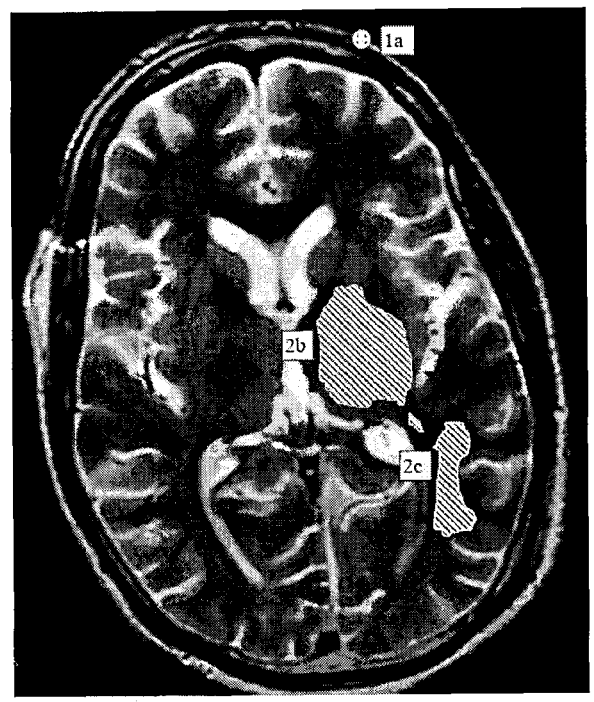
FIG. 1a illustrates an exemplary determination of possible target areas from a specified entry point of a catheter, taking into consideration catheter positioning guidelines in accordance with the invention.

FIG. 1A shows a first exemplary recording of the structure and anatomy of a brain, wherein an entry point 1a is specified, for example by a user, in the represented structure and anatomy of the brain. Possible target areas 2b, 2c of the catheter can be determined from the indicated entry point 1a and, for example, lie in such a way that catheter positioning guidelines and the structure and/or the anatomy of the brain can be taken into account when a catheter is inserted or introduced. The catheter positioning guidelines can be the distance between the catheter tip or the catheter delivery section and the surface of the brain, or the distances between the catheter, the catheter tip or the catheter delivery section and characteristic regions of the brain such as cavities, hollows, sulci, or ventricles. The target areas 2b, 2c, determined taking into consideration the catheter positioning guidelines and the individual structure and anatomy of the brain, can be represented in the recorded and represented structural and anatomical data of the brain, such that a user (e.g., a doctor or surgeon) can select the most suitable or optimal target zone 2b, 2c. Movement or positioning specifications also can be determined and, for example, shown in the represented structural and anatomical data of the brain. More particularly, the movement or positioning may be specified, for example, using vectors that describe the exact movement of the catheter so as to enable the catheter to be positioned in the brain, taking into consideration the anatomy and structure and catheter positioning guidelines.

Figure 1B:
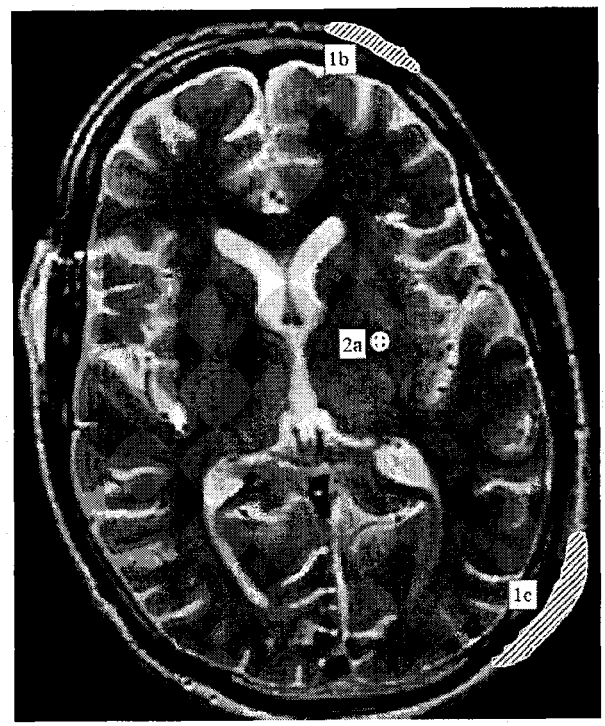

FIG. 1b shows another embodiment in which, contrary to the first embodiment, a target point 2a is specified (e.g., by a user) and entry areas 1b, 1c, associated or most suitable, taking into consideration the catheter positioning guidelines and the individual structure and anatomy of the brain, are determined, through which the catheter can be inserted or introduced into the brain.

Figure 2:
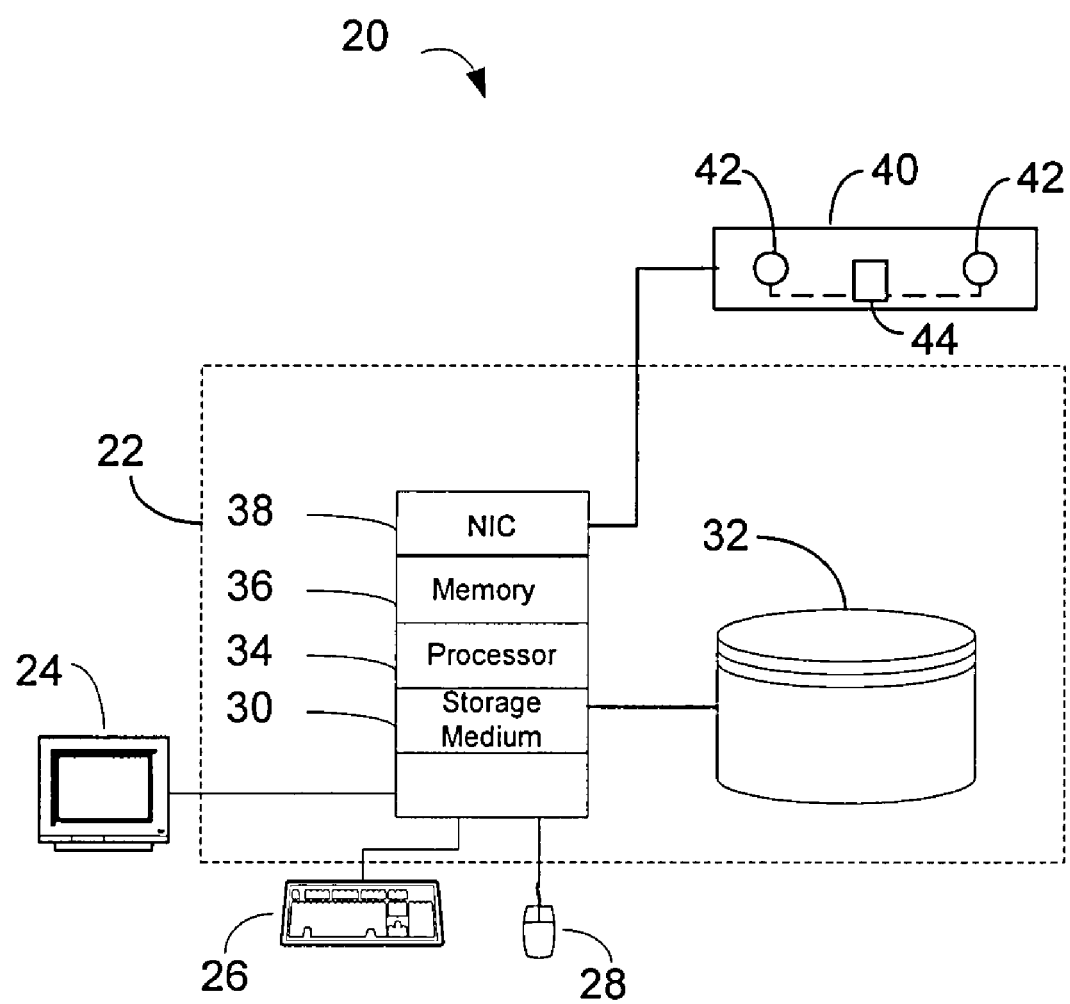
FIG. 2 is a block diagram of a computer system that can be used to implement the method of the present invention.

Moving to FIG. 2, a system 20 that may be used to carry out the method is diagrammatically illustrated. The system 20 includes a computer 22 for processing data, and a display 24 for viewing system information. The display 24 may be any type of display currently available, such as a flat panel liquid crystal display (LCD) or a cathode ray tube (CRT) display, or any display subsequently developed. A keyboard 26 and pointing device 28 may be used for data entry, data display, screen navigation, etc. The keyboard 26 and pointing device 28 may be separate from the computer 22 or they may be integral to it. A computer mouse or other device that points to or otherwise identifies a location, action, etc., e.g., by a point and click method or some other method, are examples of a pointing device.

Alternatively, a touch screen (not shown) may be used in place of the keyboard 26 and pointing device 28. A touch screen is well known by those skilled in the art and will not be described in detail herein. Briefly, a touch screen implements a thin transparent membrane over the viewing area of the display 24. Touching the viewing area sends a signal to the computer 22 indicative of the location touched on the screen. The computer 22 may equate the signal in a manner equivalent to a pointing device and act accordingly. For example, an object on the display 24 may be designated in software as having a particular function (e.g., view a different screen). Touching the object may have the same effect as directing the pointing device 28 over the object and selecting the object with the pointing device, e.g., by clicking a mouse. Touch screens may be beneficial when the available space for a keyboard 26 and/or a pointing device 28 is limited.

Included in the computer 22 is a storage medium 30 for storing information, such as a database 32 or other information (e.g., application data, screen information, programs, etc.). The storage medium 30 may be a hard drive, for example. A processor 34, such as an AMD Athlon 64® processor or an Intel Pentium IV® processor, combined with a memory 36 and the storage medium 30 execute programs to perform various functions, such as the method described herein, data entry, numerical calculations, screen display, system setup, etc. A network interface card (NIC) 38 allows the computer 22 to communicate with devices, such as navigation system 40. Navigation system 40 includes cameras 42 that detect optical radiation (e.g., light in the infra-red spectrum), and controller 44 operatively coupled to the cameras 42. Using data from the cameras, the controller can track objects in three dimensional space, as is conventional.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity. As will be appreciated, the various computer codes for carrying our the processes herein described can be embodied in computer-readable media.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining and representing at least one of possible entry and target areas for positioning catheters in an area of a patient's body on the basis of at least one of functional data, structural data and anatomical data of the area, comprising the steps of:

indicating, via a data input device communicatively coupled to a processor, at least one of a) at least one catheter entry area and b) at least one catheter target area;

determining, using the processor, at least one of a) at least one catheter target area and b) at least one catheter entry area, wherein said at least one catheter target are is determined based on
i) the at least one indicated catheter entry area, and
ii) specified catheter positioning guidelines and at least one of the functional data, structural data, and anatomical data of the area, and wherein said at least one catheter entry area is determined based on
i) the at least one indicated catheter target area, and
ii) specified catheter positioning guidelines and at least one of the functional data, structural data, and anatomical data of the area;

representing by the processor via a display device, at least one of the functional data, structural data, and anatomical data with at least one of
a) the indicated catheter entry area and the at least one determined catheter target area; and
b) the at least one indicated catheter target area and the at least one determined catheter entry area; and wherein the catheter positioning guidelines comprise at least one of
i) distances between the catheter or the catheter tips or the catheter delivery sections and the surface of the area,
ii) distances between a number of catheters or catheter tips or catheter delivery sections, and
iii) distances between the catheters or the catheter tips or the catheter delivery sections and particular tissue sections.

2. The method according to claim 1, wherein if the catheter entry area is indicated,
determining at least one possible catheter target point in the catheter target area based on the specified catheter positioning guidelines and at least one of the functional data, structural data and anatomical data of the area, wherein an optimal target point of the at least one catheter target point is displayed on the display device.

3. The method according to claim 2, wherein once the at least one possible catheter target point has been determined, determining at least one entry point inside the indicated catheter entry area and corresponding to the determined possible catheter target point based on the catheter positioning guidelines, wherein an optimal entry point of the at least one catheter entry point is displayed on the display device.

4. The method according to claim 1, wherein if the catheter target area is indicated,
determining at least one possible catheter entry point in the catheter entry area based on the specified catheter positioning guidelines and at least one of the functional data, structural data and Of anatomical data of the area, wherein an optimal catheter entry point of the at least catheter one entry point is displayed on the display device.

5. The method according to claim 4, wherein once the at least one possible catheter entry point has been determined, determining at least one catheter target point in the catheter target area and corresponding to the determined possible catheter entry point based on the catheter positioning guidelines, wherein an optimal catheter target point of the at least one catheter target point is displayed on the display device.

6. The method according to claim 1, further comprising the step of using a tissue as the catheter entry or catheter target area.

7. The method according to claim 6, wherein the step of using a tissue as the catheter entry or catheter target area includes using a brain region as the catheter entry or catheter target area.

8. The method according to claim 1, further comprising the step of using and/or determining information on tissue parts and/or on areas of tissue parts removed by operations and/or on areas of tissue deformities, tissue abnormalities or tissue anomalies, and/or on anatomical areas as functional data and/or structural and/or anatomical data.

9. The method of claim 8, wherein the tissue anomalies include oedemas and the anatomical areas include the brain stem.

10. The method according to claim 1, wherein the step of determining includes displaying on a display device at least one of the functional data, structural and anatomical data with the specified catheter positioning guidelines.

11. The method according to claim 1, wherein the step of indicating at least one catheter entry area includes indicating an entry point as the catheter entry area.

12. The method of claim 1, wherein the step of determining at least one catheter target area includes indicating a target point as the catheter target area.

13. The method according to claim 1, wherein the catheter positioning guidelines used to determine the at least one catheter target region for an indicated entry region are dependent on at least one a) of the anatomical, functional or structural characteristics of the entry region, the target region and c) the area along the trajectory of the catheter.

14. The method according to claim 1, wherein determining the catheter entry area or catheter target area based on catheter positioning guidelines includes using catheter positioning guidelines that are dependent on at least one of a) the anatomical, functional or structural characteristics of the catheter target region, b) the catheter entry region and c) the area along the trajectory of the catheter.

15. The method according to claim 1, wherein determining the catheter entry area or catheter target area based on catheter positioning guidelines includes using catheter positioning guidelines that are dependent on at least one of the respective catheter parameters, infusion parameters and infusate parameters, and further comprising using a number of consecutive infusions having the same or different infusates.

16. The method according to claim 1, wherein determining the catheter entry area or catheter target area based on catheter positioning guidelines includes using catheter positioning guidelines that are dependent on at least one of catheter trajectories already defined and on the expected area coverage from the fluids to be infused by already defined catheter trajectories.

17. The method according to claim 1, further comprising the step of determining positioning specifications based on the specified catheter positioning guidelines and at least one of the functional data, structural data and anatomical data of the area, said positioning specifications indicating how the catheter can be positioned between the at least one indicated or determined entry area and the at least one indicated or determined target area so as to be in compliance with the catheter positioning guidelines.

18. The method according to claim 1, wherein the tissue sections include grooves, furrows, sulci, chambers, ventricles, hollows, recesses, holes and/or cavities of the area.

19. The method according to claim 1, further comprising the step of using information on the surface of the area and/or on grooves or furrows, sulci or gyri of the area, furrows between cerebral convolutions, and/or on chambers, ventricles, hollows, recesses, holes and/or cavities of the area as the functional data, structural data and/or anatomical data.

20. The method according to claim 1, wherein
the distances between the catheter or the catheter tips or the catheter delivery sections and the surface of the area are between 1 and 4 cm; and/or
the distances between a number of catheters or catheter tips or catheter delivery sections are at least about 1 cm and up to about 3 cm; and/or
the distances between the catheters or the catheter tips or the catheter delivery sections and particular tissue sections are between 2 and 15 mm.

21. The method according to claim 1, wherein the catheter positioning guidelines are criteria relating to specified or defined distance characteristics of the catheter from characteristic areas or criteria relating to specified or defined distance characteristics of a number of catheters from each other or from characteristic areas.

22. A device for determining and representing at least one of possible entry and target areas for positioning catheters in an area of a patient's body on the basis of at least one of functional data, structural data and anatomical data of the area, comprising:
   a data input device for inputting at least one catheter entry area or at least one catheter target area;
   a computing device connected to the data input device, wherein if the data received by the data input device corresponds to a catheter entry area the computing unit is configured to determine at least one catheter target area based on
   i) the at least one catheter entry area, and
   ii) specified catheter positioning guidelines and at least one of functional data, structural data and anatomical data, and
   if the data received by the data input device corresponds to a catheter target area the computing device is configured to determine at least one catheter entry area based on
   i) the at least one indicated catheter target area, and
   ii) specified catheter positioning guidelines and at least one of the functional data, structural data and anatomical data;
   a database in which at least one of a) the catheter positioning guidelines and b) at least one of functional data, structural data and anatomical data is archived, wherein the database is operatively coupled to the data input device and the computing device;
   a data output device operatively coupled to the computing device for outputting at least one of a) the functional data, structural data and anatomical data, b) the specified catheter positioning guidelines, c) the at least one determined catheter target area, and d) the at least one determined catheter entry area; and
   wherein the catheter positioning guidelines comprise at least one of
   i) distances between the catheter or the catheter tips or the catheter delivery sections and the surface of the area,
   ii) distances between a number of catheters or catheter tips or catheter delivery sections, and
   iii) distances between the catheters or the catheter tips or the catheter delivery sections and particular tissue sections.

23. The device according to claim 22, comprising a medical tracking system for determining the position of the catheter and the position of the area, wherein the computing unit correlates the information on the position of the catheter and on the position of the area with the functional data and/or structural and/or anatomical data, and wherein the correlated information is represented on the data output device.

24. A computer program embodied on a non-transitory computer readable medium for determining and representing at least one of possible entry and target areas for positioning catheters in an area of a patient's body on the basis of at least one of functional data, structural and anatomical data of the area, wherein when the program is executed by a processor the program causes the processor to perform the following steps:
   receiving, via a data input device communicatively coupled to a processor, at least one of a) at least one catheter entry area and b) at least one catheter target area;
   determining at least one of a) at least one catheter entry area and b) a at least one catheter target area, wherein
   said at least one catheter target area is determined based on
   i) the at least one indicated catheter entry area,
   ii) specified catheter positioning guidelines and at least one of the functional data, structural data and anatomical data of the area, and
   wherein said at least one catheter entry area is determined based on
   i) the at least one indicated catheter target area, and
   ii) specified catheter positioning guidelines and at least one of the functional data, structural data, and anatomical data of the area;
   representing for display at least one of the functional data, structural data, and anatomical data with at least one of
   a) the at least one indicated catheter entry area and the at least one determined catheter target area, and
   b) the at least one indicated catheter target area and the at least one determined catheter entry area; and
   wherein the catheter positioning guidelines comprise at least one of
   i) distances between the catheter or the catheter tips or the catheter delivery sections and the surface of the area,
   ii) distances between a number of catheters or catheter tips or catheter delivery sections, and
   iii) distances between the catheters or the catheter tips or the catheter delivery sections and particular tissue sections.

* * * * *